United States Patent [19]
Schmidt et al.

[11] Patent Number: 5,619,186
[45] Date of Patent: Apr. 8, 1997

[54] FOOT WEIGHT ALARM

[75] Inventors: Robert N. Schmidt, Cleveland, Ohio; Richard S. Diefes, Doylestown, Pa.

[73] Assignee: Cleveland Medical Devices Inc., Cleveland, Ohio

[21] Appl. No.: 415,630

[22] Filed: Apr. 3, 1995

[51] Int. Cl.$^6$ ................................. G08B 23/00
[52] U.S. Cl. ............... 340/573; 73/172; 128/779; 340/328; 340/666
[58] Field of Search ................. 340/573, 666, 340/328, 529, 309.15; 128/779; 73/172; 364/567, 413.02; 200/85 R; 177/45, 245

[56] References Cited

U.S. PATENT DOCUMENTS

| | | | |
|---|---|---|---|
| 3,702,999 | 11/1972 | Gradisar | 340/573 |
| 3,791,375 | 2/1974 | Pfeiffer | 128/779 |
| 4,647,918 | 3/1987 | Goforth | 340/573 |
| 4,928,959 | 5/1990 | Bassett et al. | 340/573 X |
| 5,042,504 | 8/1991 | Huberti | 128/779 |
| 5,209,240 | 5/1993 | Jain et al. | 128/779 |
| 5,285,022 | 2/1994 | Antone | 177/253 |
| 5,323,650 | 6/1994 | Fullen et al. | 73/172 |
| 5,357,696 | 10/1994 | Gray et al. | 73/172 X |
| 5,408,873 | 4/1995 | Schmidt et al. | 128/779 X |
| 5,471,405 | 11/1995 | Marsh | 128/779 X |

OTHER PUBLICATIONS

Miyazaki et al., "Limb load alarm device", *Medical & Biological Engin. & Comput.*, vol. 16, No. 5, pp. 500–506, Sep. 1978.
Endicott et al., "Leg load warning system", *Medical & Biological Engineering*, vol. 12, pp. 318–320, May 1974.
Novel Electronics Inc., "Micro Emed" brochure, Aug. 1991.
Tek Scan Inc., Brochure on "FSCAN" Gait Analysis System, date unknown.
BarMed, Pty. Ltd., Brochure on "BarMed LLM–100" Portable Limb Load Monitor, date unknown.
VistaMed, Brochure on "FSA Foot Assessment System", date unknown.
Raymar, Brochure on "DPM–2000M", date unknown.
InfoTronic, Advertizement of "F.P.L. (Foot Pressure Limiter)", date unknown.

*Primary Examiner*—Thomas Mullen
*Attorney, Agent, or Firm*—Robert N. Schmidt; John H. Vynalek

[57] ABSTRACT

Device for alarming foot weight capable of operating without restricting an individual's movement. The device comprising a power supply, at least one resistive force sensor, signal conditioning means, calibrating means, programming means and alarm generating means. The alarm generating means generates an alarm when the weight applied to the foot force sensor is at, within or above at least one weight limit or weight range.

21 Claims, 1 Drawing Sheet

FOOT WEIGHT ALARM

This invention was made as a result of work under Grant 5R44 NS30279 between the U.S. Department of Health and Human Services and Cleveland Medical Devices, Inc. and the U.S. Government has rights in this invention pursuant thereto.

BACKGROUND OF THE INVENTION

The present invention relates generally to the field of foot weight alarm devices and, more specifically, to weight alarming devices capable of alarming an individual's weight without restricting the individual's movement.

More than 500,000 hip and knee replacements are performed each year in the United States. There are over 250,000 hip fractures each year, with most requiring open reduction and internal fixation. In addition, the number of multiple trauma victims with lower extremity fractures each year is substantial. Individuals who have suffered a stroke may be required during rehabilitation to relearn the ability to control their body over a relatively small base in two-legged stance. In order for an individual to effectively convalesce and rehabilitate in the above-mentioned cases, or from any other injuries or surgery to the lower extremities, it is essential that the individual effectively control the amount of weight applied to the lower extremities. Accordingly, accurate and immediate detection and communication of the weight being applied is imperative.

Detection of the weight applied to the lower extremities is achieved through the use of an external sensing device employing some type of means to convert the weight applied into a signal. Such external sensing device can be a foot force sensor attached directly to the injured person's foot or inserted in, or in some manner attached to, his or her shoe. The signal is then conveyed to a device which communicates to the injured person whether a predetermined weight limit is reached. Such communication can be in the form of a sensory alarm; either visual, audible or tactile. In this way the injured person is advised that the weight being applied to the lower extremity is below, within or above a predetermined limit or desired weight range. This informs the injured person that he or she is not providing sufficient weight to encourage healing, is providing the proper amount of weight, or is providing excessive weight and, therefore, in danger of deleteriously affecting the lower extremity and impeding convalescence or rehabilitation. The injured person can then increase or reduce the amount of weight being applied to the lower extremity.

There are a number of weight alarming devices currently known and in use. These devices communicate either an alarm "on" or "off" state based upon a single predetermined weight limit without the ability to communicate multiple weights or weight ranges, or to communicate certain percentages of a predetermined weight or weight ranges. Therefore, by the time the alarm actuates, the injured person is already at, and possibly has exceeded, the predetermined weight or weight ranges and may be sustaining damage to the lower extremity without any forewarning. Also, these devices do not communicate to the injured person that more weight should be placed on the lower extremity to encourage bone growth and healing.

Accordingly, a need exists for a device for alarming foot weight for use with a foot force sensor which overcomes the above drawbacks.

SUMMARY OF THE INVENTION

The present invention provides a device to satisfy the aforementioned needs.

Accordingly, the present invention relates to a device for alarming foot weight comprising: a power supply, which provides a regulated voltage, at least one resistive force sensor connected to the power supply, signal conditioning means, calibrating means, programming means and alarm generating means. Each resistive force sensor has a resistance which varies with the amount of weight applied to it. The signal conditioning means is connected to each resistive force sensor wherein the signal conditioning means produces a voltage-corresponding digital value which varies with the resistance of the resistive force sensor. The calibrating means connected to the signal conditioning means converts the voltage-corresponding digital value into a force-corresponding digital value so that the force-corresponding digital value corresponds to the weight to which the foot force sensor is subjected. The programming means is connected to the calibrating means and sets at least one weight limit or weight range in the calibrating means so that the calibrating means can compare the force-corresponding digital value to the weight limit. Alarm generating means generates an alarm in response to the force-corresponding digital value and when the force-corresponding digital value is below, within, or above the weight limit or weight range.

BRIEF DESCRIPTION OF THE DRAWINGS

Further features of the present invention will become apparent to those skilled in the art to which the present invention relates from reading the following specification with reference to the accompanying drawings in which.

DESCRIPTION OF THE PREFERRED EMBODIMENT

Figure 1:
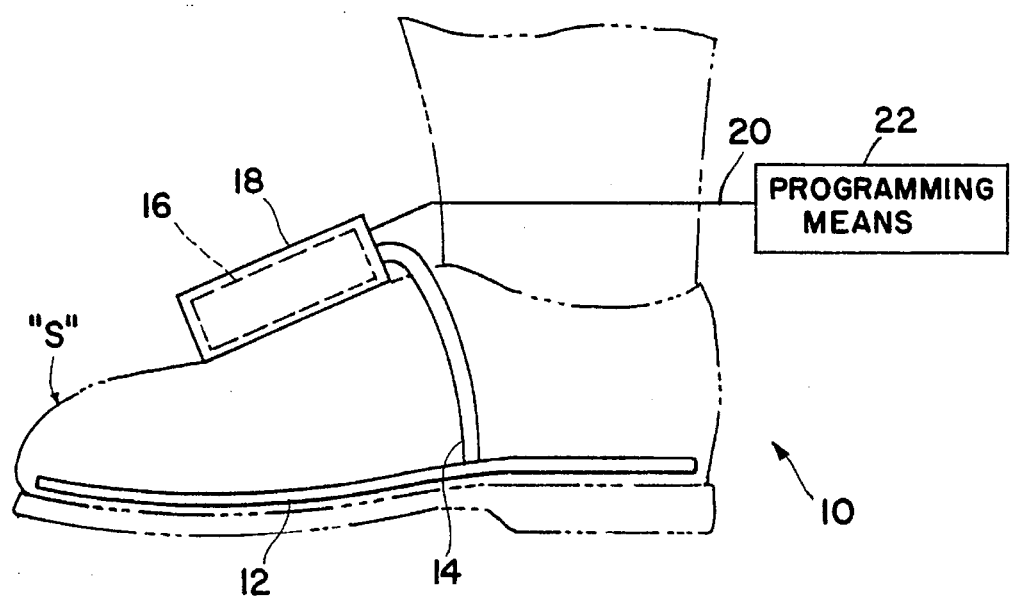
FIG. 1 is a view of a foot in a shoe showing the positioning of the foot weight alarm device on the shoe including connection to the programming means.

Referring now to the drawings and more particularly FIG. 1 there is first shown a view of an individual's foot in a shoe "S" with the foot weight alarm device 10 comprising a foot force sensor 12, a connecting means 14, a housing 16, a shoe pouch 18, a data cable 20 and a programming means 22. The foot force sensor 12 is positioned inside the shoe "S". The housing 16 is enclosed in the shoe pouch 18 which is attached to the top of the shoe "S". Advantageously, the programming means 22 is a computer and is located externally to the housing 16. The data cable 20 connects the programming means 22 to the housing 16 and, advantageously, is detachable from the housing 16 and the programming means 22.

Figure 2:
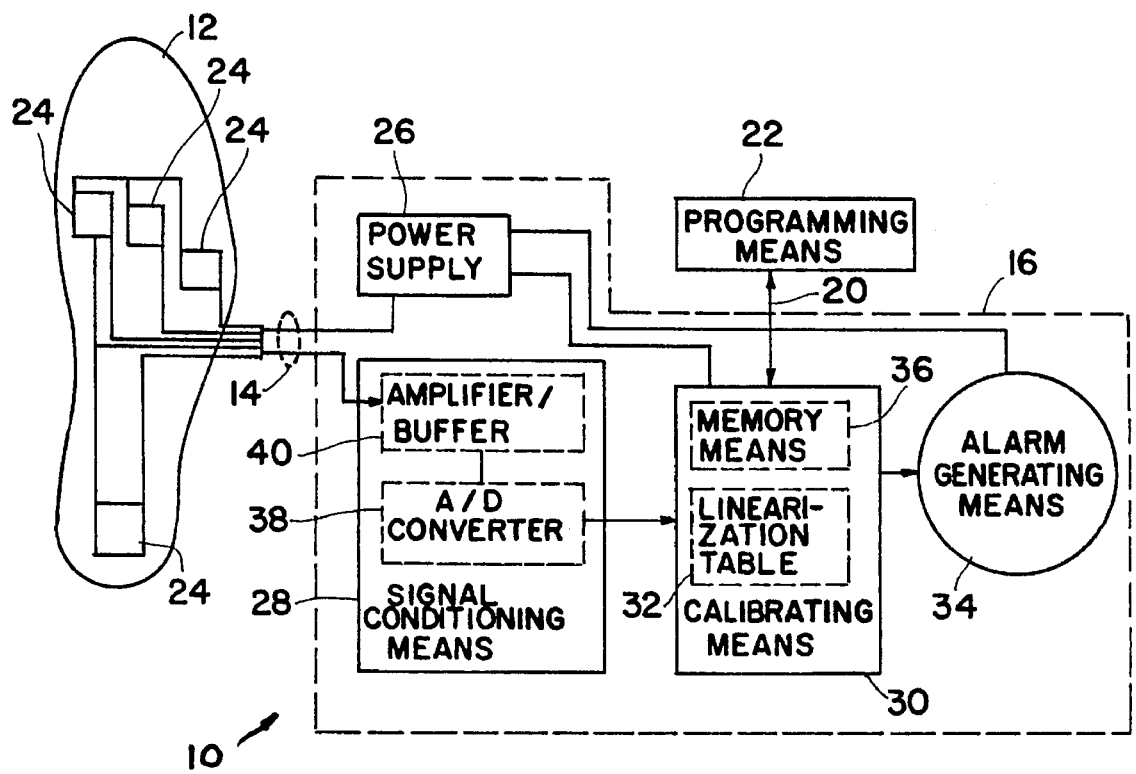
FIG. 2 is a logic diagram of the invention.

Referring now to FIG. 2, a logic diagram of the invention is shown. The foot force sensor 12 has at least one resistive force sensor 24 located thereon. In FIG. 2, a plurality of resistive force sensors 24 located in four areas of the foot force sensor 12 is shown, although it should be understood that only one resistive force sensor 24 is necessary. A power supply 26 which produces a regulated voltage is electrically connected by the connecting means 14 to each resistive force sensor 24. In the present invention, the power supply 26 is a battery and a voltage regulator. The resistance of each resistive force sensor 24 varies with the amount of weight applied to that resistive force sensor 24 which, in turn, affects the voltage drop across that resistive force sensor 24. Accordingly, the voltage drop across each resistive force sensor 24 will vary in a corresponding fashion to the amount of weight applied to that resistive force sensor 24. Each resistive force sensor 24 is electrically connected by the connecting means 14 to the signal conditioning means 28. Due to the force-varying voltage experienced across the resistive force sensor 24, a force-varying voltage is present at the signal conditioning means 28. The signal conditioning means 2% converts this force-varying voltage to a voltage-corresponding digital value. In the present invention, this is accomplished by using an analog-to-digital converter 38. Although, in the present invention, the force-varying voltage is amplified and buffered by the amplifier buffer 40 prior to being converted, it is not always necessary to do so depending upon the type of analog-to-digital converter 38 employed. The voltage-corresponding digital value varies with the resistance of the resistive force sensor 24. The calibrating means 30 converts the voltage-corresponding digital value to a force-corresponding digital value. In the present invention, the calibrating means 30 accomplishes this by comparing the voltage-corresponding digital value of each resistive force sensor 24 with a set of values programmed by the programming means 22 into the calibrating means 30 as a linearization table 32. Based upon this comparison, the calibrating means 30 determines a force-corresponding digital value for each resistive force sensor 24 which corresponds to the weight applied thereto. Linear interpolation is used for inputs falling between two values in the linearization tables 32. The force-corresponding digital value corresponds to the weight to which the resistive force sensor 24 is subjected. The force-corresponding digital values of each resistive force sensor 24 are then combined to determine a force-corresponding digital value reflective of the total weight applied to the foot force sensor 12.

The data cable 20 connects the calibrating means 30 to the programming means 22. In addition to programming the set of values utilized by the calibrating means 30 as a linearization table 32, the programming means 22 is used to set or reset at least one weight limit or weight range in units of, for example, pounds, kilograms, etc., based either on a percent of the person's body weight or on a specific unit, and to set the character of the alarm to be generated as the total weight applied to the foot force sensor 12 is below, within or above each weight limit or each weight range. When this is accomplished the data cable 20 is then disconnected from the housing 16 to allow the individual unrestricted movement. The data cable 20 can also be used to transmit data to the programming means 22 in which event the programming means 22 can be used to display and/or analyze the data transmitted.

Alarm generating means 34 generates an alarm or alarms in response to the force-corresponding digital value. The alarm or alarms can be generated when the force-corresponding digital value is below, within, or above the weight limit or weight range. Advantageously, the alarms generated may vary in volume, frequency and intermittency.

Memory means 36 records both the time and the force-corresponding digital values experienced by the resistive force sensor 24 as may be determined through the use of the programming means 22.

The invention will be exemplified in the following specific examples with the understanding that these examples are preferential and illustrative and not to be considered as limiting the invention.

EXAMPLE 1

The invention, through the programming means 22, is programmed so that the alarm generating means 34 emits a low frequency tonal alarm when a minimal amount of weight, approximately two percent (2%) of total body weight, is applied to the foot force sensor 12; a high frequency tonal alarm when the applied weight on the foot force sensor 12 reaches about fifty percent (50%) of the total body weight and until it reaches about sixty percent (60%) of total body weight; and a two (2) tone steady warble when the applied weight exceeds sixty percent (60%) of total body weight. If the weight is reduced below any one of the above-stated percentages of weight the invention resets to the corresponding alarm for the lesser weight percentage and the alarm generating means 34 will emit alarms in the same manner if the weight is increased again.

EXAMPLE 2

The invention, through the programming means 22, is programmed so that the alarm generating means 34 emits a repetitive short single-tone beep when the total amount of weight to which the foot force sensor 12 is subjected is between about forty percent (40%) and about fifty percent (50%) of total body weight; a repetitive double-tone beep between about fifty percent (50%) and sixty percent (60%) of total body weight; and a two (2) tone steady warble at more than about sixty percent (60%) of total body weight. The warble continues until the weight is reduced below sixty percent (60%) of total body weight. If the weight is reduced below any one of the percentages of weight the invention resets to the tonal alarm for the lesser weight percentage. The alarm generating means 34 will emit the alarms in the same manner if the weight is increased again.

EXAMPLE 3

Similar to EXAMPLE 1 and EXAMPLE 2 except that instead of percentages of total body weight the invention is programmed through the programming means 22 to alarm based upon certain amounts of pounds being experienced by the foot force sensor 12.

EXAMPLE 4

The invention, through the programming means 22, is programmed so that the alarm generating means 34 emits a tonal alarm when, during any two (2) hour period, the following occurs:

1. the weight applied to the foot force sensor 12 is equal to or exceeds forty (40) pounds for thirty (30) minutes; or 2. the weight applied to the foot force sensor 12 is equal to or exceeds thirty (30) pounds for forty (40) minutes; or 3. the weight applied to the foot force sensor 12 is equal to or exceeds twenty (20) pounds for fifty (50) minutes.

What is claimed is:

1. A foot weight alarm device, comprising:

a) a power supply which provides a regulated voltage;

b) at least one resistive force sensor, said resistive force sensor connected to said power supply and said resistive force sensor having a resistance which varies with the amount of weight applied to said resistive force sensor;

c) signal conditioning means connected to said resistive force sensor whereby said signal conditioning means produces a voltage-corresponding digital value which varies with the resistance of said resistive force sensor;

d) calibrating means connected to said signal conditioning means such that said calibrating means converts said voltage-corresponding digital value into a force-corresponding digital value whereby said force-corresponding digital value corresponds to the amount of weight to which said resistive force sensor is subjected;

e) programming means connected to said calibrating means whereby said programming means sets at least one weight limit in said calibrating means such that said calibrating means can compare said force-corresponding digital value to said weight limit;

f) alarm generating means which generates an alarm in response to said force-corresponding digital value; and g) a housing wherein said signal conditioning means, said calibrating means, and said alarm generating means are housed but with said programming means being external thereto.

2. The device of claim 1 further comprising a foot force sensor on which said resistive force sensor is located.

3. The device of claim 1 further comprising a data cable whereby said data cable is used to connect said calibrating means to said programming means.

4. The device of claim 1 wherein said weight limit is defined in terms of a given unit of force.

5. The device of claim 1 wherein said weight limit is defined in terms of percentage of total body weight.

6. The device of claim 1 further comprising memory means whereby said memory means records the time and said force-corresponding digital values.

7. The device of claim 6 wherein said programming means is used to program said memory means.

8. The device of claim 1 wherein said alarm varies in volume, frequency and intermittency.

9. The device of claim 8 wherein said alarm varies in volume, frequency, and intermittency depending on whether said force-corresponding digital value is below, at or above at least one weight limit.

10. The device of claim 8 wherein said alarm varies in volume, frequency, and intermittency depending on whether said force-corresponding digital value is below, at or above at least one weight range.

11. The device of claim 1 further comprising a shoe pouch into which said housing is placed, said shoe pouch constructed to allow attachment to an individual's shoe.

12. A foot weight alarm device, comprising:

a) a foot force sensor;

b) at least one resistive force sensor located on said foot force sensor, said resistive force sensor having a resistance which varies with the amount of force applied thereto;

c) a power supply which provides regulated voltage to said resistive force sensor such that a force-varying voltage is present across said resistive force sensor;

d) signal conditioning means connected to said resistive force sensor whereby said signal conditioning means comprises an analog-to-digital converter, said analog-to-digital converter converts said force-varying voltage to a voltage-corresponding digital value which varies with the resistance of said resistive force sensor;

e) calibrating means connected to said signal conditioning means whereby said calibrating means comprises a linearization table and whereby said calibrating means converts said voltage-corresponding digital value into a force-corresponding digital value by comparing said voltage-corresponding digital value to said linearization table such that said force-corresponding digital value corresponds to the amount of weight to which said resistive force sensor is subjected, and combines said force-corresponding digital value for each said resistive force sensor such that said force-corresponding digital value reflects the weight applied to said foot force sensor;

f) programming means connected to said calibrating means whereby said programming means sets at least one weight limit and said linearization table in said calibrating means such that said calibrating means can compare said force-corresponding digital value to said weight limit;

g) alarm generating means which generates an alarm in response to said force-corresponding digital value; and h) a housing wherein said signal conditioning means, said calibrating means, and said alarm generating means are housed but with said programming means being external thereto.

13. The device of claim 12 further comprising a data cable whereby said data cable is used to connect said calibrating means to said programming means.

14. The device of claim 12 wherein said weight limit is defined in terms of a given unit of force.

15. The device of claim 12 wherein said weight limit is defined in terms of percentage of total body weight.

16. The device of claim 12 further comprising memory means whereby said memory means records the time and said force-corresponding digital values.

17. The device of claim 16 wherein said programming means is used to program said memory means.

18. The device of claim 12 wherein said alarm varies in volume, frequency and intermittency.

19. The device of claim 18 wherein said alarm varies in volume, frequency, and intermittency depending on whether said force-corresponding digital value is below, at or above at least one weight limit.

20. The device of claim 18 wherein said alarm varies in volume, frequency, and intermittency depending on whether said force-corresponding digital value is below, at or above at least one weight range.

21. The device of claim 12 further comprising a shoe pouch into which said housing is placed, said shoe pouch constructed to allow attachment to an individual's shoe.

* * * * *